United States Patent
Christner et al.

(10) Patent No.: US 6,451,586 B1
(45) Date of Patent: Sep. 17, 2002

(54) ENZYME PREPARATION CONTAINING PROTEASE

(75) Inventors: Juergen Christner, Seeheim-Jugenheim; Guenter Partheil, Ober-Ramstadt; Hermann Plainer, Reinheim; Roland Reiner, Darmstadt, all of (DE)

(73) Assignee: Roehm GmbH & Co KG, Darmstadt (DE)

( * ) Notice: Subject to any disclaimer, the term of this patent is extended or adjusted under 35 U.S.C. 154(b) by 0 days.

(21) Appl. No.: 08/384,239

(22) Filed: Feb. 6, 1995

Related U.S. Application Data

(63) Continuation of application No. 08/277,705, filed on Jul. 20, 1994, now abandoned, which is a continuation of application No. 08/122,758, filed on Sep. 16, 1993, now abandoned, which is a continuation-in-part of application No. 07/783,901, filed on Oct. 29, 1991, now abandoned.

(30) Foreign Application Priority Data

Nov. 10, 1990 (DE) .......................................... 40 35 839

(51) Int. Cl.⁷ ................................................ C14C 1/00
(52) U.S. Cl. ....................................... 435/265; 435/219
(58) Field of Search ................................. 435/265, 219

(56) References Cited

U.S. PATENT DOCUMENTS

| | | | | |
|---|---|---|---|---|
| 4,009,076 A | * | 2/1977 | Green et al. | 435/187 |
| 4,087,368 A | * | 5/1978 | Borello | 435/187 |
| 4,266,031 A | * | 5/1981 | Tang et al. | 435/188 |

FOREIGN PATENT DOCUMENTS

| | | |
|---|---|---|
| DE | 30200519 | 7/1908 |
| DE | 30288095 | 10/1915 |
| DE | 21120066 | 3/1955 |
| DE | 10927464 | 5/1955 |
| DE | 10941811 | 10/1955 |
| DE | 10976107 | 2/1956 |
| DE | 31022748 | 1/1958 |
| DE | 41034317 | 7/1958 |
| DE | 20974813 | 5/1961 |
| DE | 20975095 | 8/1961 |
| DE | 21134474 | 8/1962 |
| DE | 30976602 | 1/1964 |
| DE | 20976928 | 8/1964 |
| DE | 11219620 | 6/1966 |
| DE | 31282837 | 11/1968 |
| DE | 1642619 | 1/1971 |
| DE | 2059453 | 4/1972 |
| DE | 2143945 | 3/1973 |
| DE | 12243412 | 1/1974 |
| DE | 2143945 | 3/1993 |
| DE | 0128419 | 2/2002 |
| GB | 1156900 | 7/1969 |

OTHER PUBLICATIONS

Random House Dictionary of the English Language, Random House, New York (1967), p. 1431.
Dictionary of Science and Technology, Revised Edition, Eds. Collocott et al., W & R Chambers (London?), p. 1147.
Kirk–Othmer Encyclopedia of Chemical Technology, 3rd Edn., vol. 14, John Wiley & Sons, New York, pp. 212,213.

* cited by examiner

*Primary Examiner*—Leon B. Lankford, Jr.
(74) *Attorney, Agent, or Firm*—Oblon, Spivak, McClelland, Maier & Neustadt, P.C.

(57) ABSTRACT

Powdered or granulated enzyme preparations, free of surface active agents and containing a protease as the active enzyme, wherein the protease is present as a tannin complex, with the proviso that the enzyme preparation consists of at least 50 percent by weight and up to 99.9 percent by weight of one or more conventional diluent salts. Methods for soaking and bating skins and hides using such preparations.

8 Claims, No Drawings

ENZYME PREPARATION CONTAINING PROTEASE

This application is a continuation of Ser. No. 08/227,705 filed Jul. 20, 1994 which is a continuation of Ser. No. 08/122,758 filed Oct. 29, 1991 which is a continuation-in-part of application Ser. No. 07/783,901 filed Oct. 29, 1981, abandoned.

The present invention pertains to solid enzyme preparations, free of surface active agents, containing proteases, obtained by tanning precipitation, as the active enzyme, and to methods for the soaking, bating, and unhairing of hides in the preparation of leather.

State of the Art

The technique of tannin precipitation has been known for a long time as an occasionally used method variant for the isolation of enzymes from solutions, e.g. from plant juices or aqueous culture media. There is a relatively broad state of the art relevant thereto (cf., e.g., GB-C 1,156,900, DE-A 1,642,619). As a rule, the goal is purification of the enzyme. The addition of gelatin, or working in an acid pH region (pH 3–5) serve as measures assisting good precipitation. However, because tannin disrupts further enzyme processing—after all, it forms an insoluble complex with the enzymes, whereupon they precipitate—it must again be removed, which is usually done by treating the precipitate with organic solvents, e.g. with acetone or ethanol, or by the addition of surface active agents, or by an increase in the pH value of the tannin precipitation. These are all measures which generally can be performed only on a laboratory scale without considerable complications.

Technical use of the tannin complex itself has been described in only a few cases. Thus, a tannin complex together with skim milk is said to be worked up by drying into a stable α-amylase preparation (CS 141,233). For medical use, an insoluble pancreas preparation is provided which was prepared by precipitation of pancreas with tannic acid. The preparation is insoluble in acid stomach juice, but develops its effect in the alkaline intestinal regions. (DE 128,419).

Further, DE-A 2,143,945 describes "water-insoluble, dried enzyme adducts which are compatible with the skin", inter alia in the form of tannin complexes. For practical use, the incorporation directly into a washing powder of an adduct of a bacterial protease obtained by tannin precipitation is proposed, for example. Since the tannin complex is said to be fully effective as a washing agent during use, i.e. in the washing float, it must "break up".

Problem and Solution

As is evident from the foregoing picture of the state of the art, the method of tannin precipitation of enzymes from an aqueous milieu is, to be sure, a useful precipitation technique, but the relative stability of precipitated enzyme-tannin complexes under the conditions prevailing in potential uses, seems—apart from the exceptions named—to stand in the way of their industrial utilization.

Heretofore, ammonium sulfate or sodium sulfate have preferably been used for precipitation from the juice of pressed pancreas or from bacterial cultures (cf. *Ullmanns Encyclopädie der technischen Chemie*, 4th edition, volume 10, pages 475–561, page 495 ff., Verlag Chemie, 1975; DE-A 2,234,412).

However, this procedure is by no means ideal— particularly from an ecological viewpoint—since as a rule it incurs a quite considerable loading of the waste water. This is evident from the rule of thumb which says that 50 kg of ammonium sulfate are necessary for precipitation for each 100 liters of juice containing enzyme. Such a salt load is strictly contrary to the present tendency of waste water technology to restrict sulfate loading as much as possible. Rather, an efficient method for precipitating enzymes was to be strived for, in which the waste water loading would be considerably less—as well as, also, more cost effective, particularly in view of the quite particular cost pressure under which the leather industry operates. It has now been found that the proteinase preparation according to the invention comes very close to the aforementioned technical conceptions. The invention pertains to a solid, i.e. powdered or granulated, enzyme preparation essentially free of surface active agents and containing a protease—obtained as a tannin complex by precipitation of the active enzyme from an aqueous medium by the addition of tannin—with the proviso that the enzyme preparation containing at least 50 percent by weight, preferably more than 80 percent by weight, and up to 99.9 percent by weight, of one or more salts conventionally used as extenders or diluent in commercial enzyme preparations.

By "tannins" are meant according to the present invention the polyphenols, as a rule of natural origin, encompassed under this name, particularly the tannic acids. (More exact data are found in Ullmann, *Encyclopädie der Tech. Chemie*, 3rd edition, volume 11, pages 593–594; Kirk-Othmer, *Encyclopedia of Chemical Technology*, 2nd edition, volume 12, pages 319–325, J. Wiley 1967; *Fortschritte der Chemie organischer Naturstoffe*, Zechmeister, editor, volume 41, 1–46, Springer Verlag).

By "proteases" are to be understood the enzymes included under E.C.3.4. (Cf. Kirk-Othmer, *Encyclopedia of Chemical Technology*, 3rd edition, volume 9, pages 173–223, J. Wiley 1980; E. Pfleiderer and R. Reiner in H. J. Rehm & G. Reed, *Biotechnology*, volume 6b, pages 729–742, VCH 1988; K. Aunstrup in *Industrial Aspects of Biochemistry*, B. Spencer, editor, volume 30(I), pages 23–46, North Holland 1974).

Various sub-criteria are applied, among them differentiation according to origin:

a) animal origin, such as
  α) rennin (E.C.3.4.23.4)
  β) pancreas proteases
    pancreatin, particularly trypsin; chymotrypsin (pH region of efficacy ca. 7–10); pepsin (E.C.3.4.23.1) (pH region of efficacy ca. 1.5–4.0; cathepsin (E.C.3.4.23.5) (region of efficacy ca. 4.0–5.0)
b) plant origin
  α) papain (E.C.3.4.22.1) pH region of efficacy ca. 5.0–8.0
  β) ficin (E.C.3.4.22.3) pH region of efficacy ca. 4.0–9.0
  γ) bromelin (E.C.3.4.22.4 and 3.4.22.5) pH region of efficacy ca. 5.0–7.0
c) microbial origin (cf. L. Keay in *Process Biochemistry* 1971, pages 17–21)
  α) from Bacillus species
    such as *B.subtilis, B.licheniformis, B.alkalophilus, B.cereus, B.natto, B.vulgatus, B.mycoides*
  β) from Streptococcus species
  γ) from Streptomyces species
    such as *Streptomyces fradiae, S.qriseus, S.rectus*
  δ) from Aspergillus species
    such as *Aspergillus flavus-oryzae, A.niger, A.saitoi, A.usamii*
  ε) from Mucor and Rhizopus species
    such as *Mucor pusillus, M.miehei*

ζ) Endothia species
such as *Endothia parasitica*
η) from Trametes species
such as *Trametes sanquinea*.

Besides this differentiation according to origin, differentiation according to the kind of attack (exo- versus endo-enzymes) and on the basis of the "active site" of the proteases (serine proteases, which are inhibited by diisopropylfluorophosphate, sulfhydryl enzymes) is also used.

Further, the pH dependence of the enzyme activity is of considerable practical significance. Here, differentiation is, above all, according to practical criteria.

i) alkaline proteases, having an activity optimum about in the region from pH 7.5 to 13,
particularly alkaline bacterial proteases (E.C.3.4.21.) (which mostly belong to the serine type) and alkaline fungal proteases ii) neutral proteases, having an activity optimum in the range from pH 6.0–9.0,
particularly neutral bacterial proteases (E.C.3.4.24) (which belong to the metalloenzymes) and fungal proteases, for example Bacillus proteases, Pseudomonas proteases, Streptomyces proteases, Aspergillus proteases iii) acid proteases, having an activity maximum in the range from pH 2.0–5.0 (E.C.3.4.23)
particularly acid fungal proteases, e.g. from Rhizopus species, Aspergillus species, Penicillium species, Mucor species, and *Impex lacteus* and *Endothia parasitica*.

Subtilisins, alkaline bacterial proteases of the serine type which are stable in the pH region 9–10 and are to some degree insensitive to perborate, are especially mentioned as alkaline proteases.

The use of proteolytic enzymes is an established part of leather manufacture, particularly in the beamhouse, since the introduction of enzymatic bating (tryptic digestive enzymes of the pancreatic gland) in the "OROPON" bate by Dr. Otto Röhm (DE-PS 200,519) about 80 years ago. In addition to use in the bate (DP-PS 927,464; DE-PS 976,107; DE-PS 941,811; DE-PS 974,813; DE-PS 975,095; DE-PS 976,928; DE-PS 1,120,066;DE-PS 1,134,474; DE-PS 1,219,620; DE-PS 1,282,837; U.S. Pat. Nos. 3,939,040; 4,273,876) enzyme preparations are also used in soaking (DE-PS 288, 095; DE-PS 976,662; DE-PS 1,022,748; DE-PS 1,034,317; DE-PS 1,282,828; DE-PS 2,059,453; U.S. Pat. Nos. 4,278, 432; 4,344,762), as well as in hair loosening and hide opening (U.S. Pat. No. 4,294,087).

The proteolytic efficacy of enzymes is commonly determined according to the Anson hemoglobin method [M. L. Ansen, J. Gen. Physiol. 22, 79 (1939], or as "LVE" (L öhlein-Volhard Units) according to the Löhlein-Volhard method (Die Löhlein-Volhard'sche Methode zur Bestimmung der proteolytic Activität", *Gerberiechem. Taschenbuch*, Dresden-Leipzig, 1955). One L öhlein-Volhard unit is defined as that amount of enzyme which digests 1.725 mg of casein under the specific conditions of the method (cf. R. J. Beynon, J. S. Bond, *Proteolytic Enzymes*, IRL Press).

Further in the following, units derived from the Anson method are used for the determination of the activity of enzymes effective in the acid region. These units are designated "proteinase units (Hemoglobin)", $U_{Hb}$. One $U_{Hb}$ corresponds to that amount of enzyme which catalyzes the liberation from hemoglobin of fragments, soluble in trichloroacetic acid, equivalent to 1 $\mu$mol of tyrosine per minute at 37° C. (measured at 280 nm). (1 $mU_{Hb}=10^{-3}$ $U_{Hb}$).

As already mentioned, the preparation of the proteinase preparation according to the invention advantageously proceeds directly from aqueous culture media or juices containing enzymes.

The winning of the preparation from the pancreas is of special interest.

A. Winning from the pancreatic complex

The techniques of the invention can partially utilize isolation methods of the prior art (cf. Ullman, op.cit., 4th edition, volume 10, pages 536–537.)

Isolation advantageously proceeds from pancreatic glands directly after slaughter, predominantly of swine or cattle.

For example about 100 pancreatic glands can be worked up in one batch by removing fat and connective tissue from the glands as completely as possible immediately after slaughter and then homogenizing the gland tissue, e.g. using a mincing machine. Immediately thereafter, extraction follows, suitably with about double the volume (about 60 liters) of 0.25 N sulfuric acid at 5° C. for 18–24 hours. After the addition of filter flakes, the extract is filtered, preferably using a packing press.

The largely fat-free liquid of the pressings obtained in this way is the starting material for isolation of the protein preparation.

B. Winning from other aqueous crude extracts containing proteinase

Instead of the liquid from pancreas pressings, other protein-containing culture liquids, e.g. of fungal or bacterial cultures, can be used (cf. the prior teachings concerning the source of enzyme as well as Ullmann, op. cit., 4th edition, volume 10, pages 518–522; *Biotechnology*, H. J. Rehm and G. Reed, editors, volume 7a, pages 156–168, Verlag Chemie 1987).

The culture liquids contain—as an approximate reference point—between 0.01 and 3 percent by weight of protein.

The proteases of the invention can be recovered as solid enzyme products in the form of a powder or granulate containing an effective enzyme and free of surface active agents as follows:

First, the correct dosage of the precipitating agent has proved to be important. If a deficient amount of tannin is used, the precipitation is incomplete; with an excess of tannin, the tannin complex is broken up only with difficulty.

As a convenient technical rule, it has turned out that just so much precipitant should be used that 0.5–3 percent of the enzyme activity originally present before the addition of tannin is still found in the supernatant. Thus, for example, for precipitation from pancreas liquid pressings (containing about 2 percent by weight of active protein), 4 percent by weight of mimosa tannin is used. In general, the protein content in the tannin complexes is from 10 to 80 percent by weight.

More in detail, one advantageously proceeds such that an aqueous liquid having a low pH value is prepared (to be sure, attention must be paid to the stability of the proteases involved). As a reference point, a pH value of about 3–6 is mentioned: Culture or pancreas liquids mostly have a pH value of about 6. Precipitation above pH=7 is less advantageous. In every case, it is advantageous to use low temperatures (20° C. or below). Also, the addition of water soluble surface active agents having an HLB value less than 6 has proved favorable. Such surfactants are chosen, for example, from the class of long-chain esters, such as the sorbitan fatty acid esters for instance. Sorbitan monooctadecanoate, for example, can be mentioned inter alia. Such surfactants are commercially available, cf. products of Atlas Chemie, Essen, of the "SPAN" type, for example.

By definition, a salt content of at least 50 percent by weight is present in the enzyme preparation, consisting of one or more salts conventionally used as diluents. These salts may be, preferably, ammonium sulfate or sodium sulfate, for example.

Advantageous Effects

Advantageous effects are already noted from the point of view of preparation and availability, but not last are such effects in the use of the enzyme preparation of the invention. The preparation of the tannin complexes involves a very good utilization of resources, because it involves both an effective and at the same time selective precipitation method. The considerably lower environmental pollution by the "mother liquor", when compared with the salt precipitations most often performed, is emphasized. The enzyme preparations can be classed as "advanced" from the point of view of work-place hygiene because they are not dust forming and have scarcely any allergenic effect on the skin.

From the point of view of uses, it can be considered an advantage that the enzyme preparations according to the invention can be used within the traditional technical procedures, i.e. there is no basic change necessary in the course of treatment in the beamhouse. The use of the enzyme preparation according to the invention has proved valuable particularly in the course of the traditional enzymatically-assisted soaking and in the bate. In such treatments, the presence of a high pH value during use is particularly advantageous (pH>8) because such favors the "breaking up" of the tannin complexes.

When used in soaking, the preparations of the invention bring about a faster rehydration of salt-conserved hides. When used in bating, the preparations of the invention effect a better removal from the hide surface of pigment residues and hair roots.

Use: Soaking

The soaking of hide material, by which the hardening of the hide which occurs because of salt preservation is reversed, is usually carried out at a pH>7 to 10. The joint use of enzymes, particularly of proteolytic enzymes, accelerates the soaking effect by "digestion" of the water soluble and other protein bodies which do not belong to the collagenous fibrous structure of the hide. In general, in soaking, enzymes having an effective range (or pH optimum of the proteolytic effect) at a pH 7.0–10.0 are used. By the removal of non-collagenous proteins, a more rapid and more intensive wetting of the hide is assured. Advantageously, the soak water is made alkaline (see supra), but the pH value should always remain<12. Additionally, soaking auxiliaries such as nonionic and anionic surfactants in combination with substituted phenols or dithiocarbamates in the usual concentration ranges (0.1–10 g/l) are advantageous. As enzymatic additives in the enzyme formulations according to the invention, the aforementioned proteases, for example, particularly the proteases mentioned under c) come into consideration, especially microbial proteases in the active range of 7–11.0, particularly Bacillus proteases, Streptomvces proteases, as well as fungal proteases, e.g. from Aspergillus species like *A.saitoi* and *A.usamii*, also such as from *A.oryzae* having a activity region of pH 7.0–9.5, and also from *A.niger* and *A.flavus* having a range of pH effectiveness at 9.5–11.0.

In general, the concentration of proteolytic activities of the proteinases employed is in the range from 0.1–0.3 Anson units, or 10,000 to 30,000 Löhlein-Volhard units per liter of soaking bath. The amounts of enzyme preparation added thus correspond to these concentrations, depending on the measure of their enzyme content. Finally, the soaking baths may additionally contain amylases. The amylases occur, e.g., as accompanying enzymes of fungal proteases. They improve the cleavage of glycosidic bonds in the proteoglycans and glycoproteins of the hide.

In the processes of the beamhouse, liming as a rule follows the soak, followed by deliming and the—predominantly enzymatic—bate.

The enzyme preparation can also be employed to advantage in these subsequent steps.

Use: Bating

Deliming traditionally serves to reduce the alkalinity of the unhaired hides from pH values of 13–14 to pH values in the region from 7–8. For deliming, strongly dissociated acids should preferably not be used, but rather weak organic acids, e.g. of the dicarboxylic acid type, or weakly acid salts. In bating, residues of epidermis, hair, and pigment are to be removed and an additionally opening of the hide effected. Further, non-collagenous protein residues are removed (cf. Ullmann, op.cit., 4th edition, volume 16, pages 119–120). Bating conventionally proceeds at a pH of 7.5 to 8.5. The use of cyclic carbonates in deliming is known from DE-A 3,108,428.

The amount of protease employed in the bate liquor is from 5,000 to 20,000 Löhlein-Volhard units per liter.

Lipases can concurrently be used in the bate, for example pancreas lipases having an activity region at pH 7.0–9.0. Also amylases according to A., for example pancreas amylases, having an activity region at pH 5.5–8.5, which favor the cleavage of glycosidic bonds in the bate, have a favorable influence on bating (above all as accompanying enzymes of trypsin and chymotrypsin).

The following Examples serve to illustrate the invention.

EXAMPLES

Example 1

Manufacture of a Preparation from Pancreas 100 kg of the filtrate from defatted pancreatic glands containing 1.4 percent of protein are combined by stirring at room temperature with a solution of 5 kg of tannin from mimosa in 20 kg of water. The precipitation of the protein, which begins immediately, is stirred further for 2 hours at room temperature (20° C.) and is then filtered. The filter cake is pressed in a packing press and then somewhat broken up into smaller pieces. Then it is dried protectively at temperatures of 60–80° C. and mixed with ammonium sulfate in a ratio by weight of 1:10.

The mixture so obtained can be used directly in the soaking of leather, for bating, for unhairing, and for the loosening of wet blues.

Example 2

Manufacture of a Preparation from an *A.orvzae* Fermentation

A protease concentrate containing about 2 percent of protein is obtained from a fungus culture by ultrafiltration and is cooled to +15° C. 100 kg of the concentrate are then combined with 4 kg of mimosa tannin in 16 kg of water. Precipitation of the protein begins immediately. After standing for 1 hour, and after addition of 2 kg of a filtering auxiliary comprising perlite ("DICALITE 4408", Dicalite Co., Neuss), the batch is filtered (60–80 liters per hour and square meter of filter area). The pressed filter cake is carefully dried (60–80° C.) and mixed in a ratio by weight of 1:30 with a mixture of sodium sulfate and ammonium sulfate.

The mixture obtained can be employed directly in leather soaking, in bating, for unhairing, and for loosening wet blues.

Example 3

Use of the Preparation of the Invention for Soaking and Bating

A preparation according to the invention was prepared as in Example 1 with the difference that the protein, precipitated with tannin from mimosa, was admixed with ammonium sulfate in a weight ratio of 1:25. That is, the final composition contained 4 percent by weight of active protein/tannin complex and 96 percent by weight of ammonium salt. The complex/salt preparation had an enzyme activity of 8500 Löhlein-Volhard units (LVU) per gram, corresponding to an activity of the pure enzyme of 212,500 LVU/g.

The activity of a 1 percent solution by weight of this mixture in tap water showed 85 LVU/g of solution, corresponding to a recovery of the original protein of 100 percent in the aqueous solution, or a complete dissociation of the enzyme/tannin complex.

For use in soaking and bating, this solution was further diluted 1:5 with water so that the bath contained 17,000 LVU/l.

For soaking, the bath and cowhides were combined at a ratio of 1:1, i.e. one liter of the bath was combined with one kilogram of hides. The pH value was adjust to 10 with soda and soaking continued for 4 hours at 30° C. in the absence of any other additives. When used for soaking, there was a good softening effect, indicating a high uptake of water by the hides.

For use as a bate, the aqueous bath again was used in an amount of 1 liter per 1 kg of cowhides. The pH was adjusted to 8.0 with a mixture of aliphatic and aromatic dicarboxylic acids commercially available as DERMASCAL ASB®. The bath, which was used for 1.5 hours at 30° C. in the absence of any other additives, gave good loosening and removal of ground.

Example 4

Use of Enzyme/Tannin Complex without Added Salt for Soaking and Bating

Again, a protein/tannin complex was prepared as in Example 1 but the complex was not admixed with a salt. Rather, the complex, which again had an enzyme activity of 212,500 LVU/g, was dissolved in tap water to give an aqueous solution containing 0.04 percent of the complex. Measurement of the enzyme activity of this solution gave a value of only 30 LVU/g instead of the expected 85 LVU/g, indicating that, despite the high degree of dilution involved, the enzyme/tannin complex was not completely dissociating.

When again diluted with water in a ratio of 1:5 and used as a bate at a ratio of float to hide of 1:1 under the conditions described above, this aqueous solution gave a barely noticeable loosening of ground. When soaking under the conditions described above, the softening effect is very slight.

What is claimed is:

1. A powdered or granulated enzyme preparation, free of surface active agents, consisting of 80 to 99.9 percent by weight of at least one salt, otherwise conventionally used as a diluent, the remainder being a protease, present in the preparation in inactive form in a tannin complex from which it is released in active form by the salt when the preparation is dissolved in water.

2. An enzyme preparation as in claim 1 wherein the salt is at least one member selected from the group consisting of ammonium sulfate and sodium sulfate.

3. In a method of soaking hides in a soaking float in the presence of a proteolytic enzyme, the improvement wherein the enzyme is added to the soaking float as the enzyme preparation of claim 1 to give a proteolytic activity from 10000 to 30000 Löhlein-Volhard units per liter of soaking float.

4. A method as in claim 3 to wherein the float has an initial pH value of 7 to 11.

5. A method as in claim 4 wherein the initial pH value is 8 or greater.

6. In a method of bating hides in bate liquor in the presence of a proteolytic enzyme, the improvement wherein the enzyme is added to the bate liquor as the enzyme preparation of claim 1 to give a proteolytic activity from 5000 to 20000 Löhlein-Volhard units per liter of bate liquor.

7. A method as in claim 5 wherein the bate has an initial pH value of 5 to 11.

8. A method as in claim 7 wherein the bate has an initial pH value of 6 to 9.

* * * * *